(12) United States Patent
Bettencourt-Silva et al.

(10) Patent No.: US 11,177,025 B2
(45) Date of Patent: Nov. 16, 2021

(54) INTELLIGENT RECOMMENDATION OF USEFUL MEDICAL ACTIONS

(71) Applicant: INTERNATIONAL BUSINESS MACHINES CORPORATION, Armonk, NY (US)

(72) Inventors: Joao H. Bettencourt-Silva, Dublin (IE); Vanessa Lopez Garcia, Dublin (IE); Natalia Mulligan, Dublin (IE); Marco Luca Sbodio, Castaheany (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 196 days.

(21) Appl. No.: 16/013,913

(22) Filed: Jun. 20, 2018

(65) Prior Publication Data
US 2019/0392924 A1    Dec. 26, 2019

(51) Int. Cl.
| | | |
|---|---|---|
| *G16H 10/60* | (2018.01) | |
| *G16H 50/70* | (2018.01) | |
| *G16H 50/20* | (2018.01) | |
| *G16H 50/50* | (2018.01) | |
| *G16H 50/30* | (2018.01) | |

(52) U.S. Cl.
CPC ............. *G16H 10/60* (2018.01); *G16H 50/20* (2018.01); *G16H 50/70* (2018.01); *G16H 50/30* (2018.01); *G16H 50/50* (2018.01)

(58) Field of Classification Search
CPC ........ G16H 10/60; G16H 50/70; G16H 50/20; G16H 50/30; G16H 50/50; G16H 20/00; G16H 70/40

USPC .......................................................... 705/2–3
See application file for complete search history.

(56) References Cited

U.S. PATENT DOCUMENTS

| | | | |
|---|---|---|---|
| 8,645,165 B2 | 2/2014 | Belcher et al. | |
| 2010/0174555 A1 | 7/2010 | Abraham-Fuchs et al. | |
| 2012/0016690 A1* | 1/2012 | Ramarajan ............. | G16H 50/20 705/2 |
| 2012/0232930 A1 | 9/2012 | Schmidt et al. | |
| 2015/0025908 A1* | 1/2015 | Lakshminarayan ... | G16H 10/60 705/3 |
| 2016/0224760 A1 | 8/2016 | Petak et al. | |
| 2017/0277854 A1 | 9/2017 | Kelley et al. | |
| 2018/0060501 A1 | 3/2018 | Gunjan | |
| 2018/0060503 A1* | 3/2018 | Allen ..................... | G16H 50/20 |

(Continued)

OTHER PUBLICATIONS

O'Connor et al., "Strategies to Prioritize Clinical Options in Primary Care," Annals of Family Medicine, vol. 15, No. 1, Jan./Feb. 2017 (4 pages).

*Primary Examiner* — Jonathan Durant
*Assistant Examiner* — Benjamin L. Hanks
(74) *Attorney, Agent, or Firm* — Griffiths & Seaton PLLC (57) ABSTRACT

Embodiments for intelligent recommendation of useful medical actions to a user by a processor. One or more useful medical actions may be cognitively recommended with evidence in support thereof for impacting a health state of a user according to historical data collected from one or more data sources, one or more user profiles, a domain knowledge, feedback data, or a combination thereof. The one or more useful medical actions may be ranked according to a scoring criteria, the domain knowledge, the historical data, a set of rules, previously recommended medical actions, or a combination thereof.

17 Claims, 6 Drawing Sheets

(56) References Cited

U.S. PATENT DOCUMENTS

2018/0322953 A1* 11/2018 Schmidt .................. G16H 50/70
2020/0043612 A1*  2/2020 McNair .................. G16H 10/60

* cited by examiner

INTELLIGENT RECOMMENDATION OF USEFUL MEDICAL ACTIONS

BACKGROUND OF THE INVENTION

Field of the Invention

The present invention relates in general to computing systems, and more particularly to, various embodiments for intelligent recommendation of useful medical actions by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize impacts on a health state or health of a person.

SUMMARY OF THE INVENTION

Various embodiments for intelligent recommendation of useful medical actions to a user using one or more processors, are provided. In one embodiment, by way of example only, a method for intelligent recommendation of useful medical actions, again by a processor, is provided. One or more useful medical actions may be recommended at a selected time period for positively impacting a health state of a user according to historical data collected from one or more data sources, one or more user profiles, a domain knowledge, feedback data, a confidence score, or a combination thereof. The medical actions may include a clinical action, nursing activities, patient-care assistance, cleaning actions, actions impacting a health state of the user, or a combination thereof. The one or more useful medical actions may be refined according to the feedback data collected from a machine learning operation, a domain knowledge expert, or a combination thereof.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices", which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user such as, for example, a medical patient. For example, as the demand for, and access to, data continues to expand in society, consumers of information content, particularly individuals desiring to make well-informed decisions regarding a medical condition or health state of a patient, continue to increase. The openness of the internet, with the ever-increasing availability of a variety of types of computing devices (e.g., IoT devices) and the cloud computing environment for viewing, interacting, or engaging with information, provides the ability of users to have continuous access to information content relating to a variety of settings.

Accordingly, the present invention provides for automatically determining a usefulness of one or more medical actions for a patient (e.g., treatment, assessment, routine, behavior modification, etc.) at a selected time, which may be based on 1) historical data from different data sources (e.g., electronic medical records ("EMBs"), habits, activities of daily living ("ADL")), and 2) collected feedback from one or more domain knowledge experts and/or machine learning operations relating to one or more previous results determined for similar cases relating to the patient, other patients, or a combination thereof.

For example, the present invention may be employed within healthcare domains such as, for example, Clinical Decision Support Systems ("CDSS"), Computerized Physician Order Entry ("CPOE"), and/or medical/clinical decision making applications. The CDSS may analyze data to support healthcare providers making clinical decisions, including the education of junior clinical staff and evidence based medicine. The CPOE may replace a hospital's paper-based ordering system allowing users to electronically write a full range of orders, maintain an online medication administration record, and review changes made to an order by successive personnel. The CPOE also offers safety alerts that are triggered when an unsafe order (such as for a duplicate drug therapy) is entered, as well as clinical decision support to guide caregivers to less expensive alternatives and/or to clinical choices that better fit established hospital protocols. In one aspect, the medical/clinical decision application includes a cognitive process for selecting one or more courses of action in the context of health or medical diagnosis and treatment.

In an additional aspect, various mechanisms of the illustrate embodiments build a recommendation model by leveraging heterogeneous historical input data about both a single patient and also a population of patients (e.g., a selected number of patients). Such heterogeneous data may also include non-medical data such as, for example, contextual data, social factors, behavior patterns and/or habits, and/or ADLs. In one aspect, the present invention progressively refines the recommendation model by taking into account feedback from one or more domain knowledge experts, a machine learning operation, or a combination thereof. The feedback may include approvals, rejections, and/or rankings of previous recommendations. Thus, the system for intelligent recommendation of usefulness medical actions provides an interactive responsive system that reacts when a domain knowledge expert decides on one or more medical actions for a patient and suggests more optimal alternative when available. A machine learning mechanism may use the heterogeneous historical input and/or feedback information to build the recommendation model and also learn the health state of one or more patients.

In one aspect, the feedback data may also be collected from one or more IoT devices or sensors such as, for example, smart phones, wearable devices or sensors (e.g., proximity sensors, cameras, radio frequency identification "RFID" readers, biometric sensors, wearable sensors, and the like.). Also, as used herein, sensors may include proximity sensors, cameras, radio frequency identification "RFID" readers, biometric sensors, wearable sensors, computers, handheld devices (e.g., Global Positioning System "GPS" device or step counters), smart phones, and/or other sensor based devices.

In an additional aspect, the present invention provides an intelligent medical advice recommendation system. One or more useful medical actions may be recommended at a selected time period for positively impacting a health state of a user according to historical data collected from one or more data sources, one or more user profiles, a domain knowledge, feedback data, a confidence score, or a combination thereof. The medical actions may include a clinical action, nursing activities, patient-care assistance, cleaning actions, actions impacting a health state of the user, or a combination thereof. The one or more useful medical actions may be refined according to the feedback data collected from a machine learning operation, a domain knowledge expert, or a combination thereof.

The term "usefulness" or "useful" as used herein may refer to one or more medical actions having a positive impact upon a patient, one or more medical actions that increases and/or improves a patient's health state, and/or one or more defined purposes, actions, and/or efforts. Useful may be generally defined as the ability to be used for a practical purpose, capable of being put to use, serviceable for an end or purpose, and/or having value or productivity. Useful may also be defined as one or more medical actions that reduce unnecessary, non-useful, unsafe, or ineffective medical actions performed on a patient, reduce an overall cost, and increase productivity of healthcare and/or a health state of a patient. Useful medical actions may also include those medical actions that protect a patient from unnecessary, unsafe, and/or ineffective medical actions.

In one aspect, the health state may include at least one or more medical conditions of one or more users, a health state (e.g., subjective health state "SWB", emotional health state, mental health state, physical health state, or an overall health state) of the one or more users, an emotional state of the one or more users, biometric data, behavior patterns, a health profile of the user, or a combination thereof. In one aspect, health state may be generally described as a normal/standardized or satisfactory condition of existence of the user or a state characterized by health, happiness, emotional stability, mental stability, physical stability, or success. As one of ordinary skill in the art will appreciate, "health state" may be dependent on a number of factors, including such factors as medical condition, emotional stability, mental stability, physical stability, financial stability, a degree or level of happiness, or other factors that may be learned. A health state of a user/patient may be defined. For example, a knowledge base or ontology may be used to define a health state for a user/patient and may include defining and/or indicating one or more correlations between a health state, a plurality of states, medical conditions, activities of daily living (ADL), and context of daily living (CDL).

Moreover, as used herein, ADLs may refer to the most common activities that people perform during a day. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADLs may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A knowledge domain may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed. In one aspect, the ADLs for a person may be learned such as, for example, using machine learning or using a knowledge domain relating to information about the person's activities and behaviors. The machine learning may provide a predictive model that may analyze, determine, identify, and/or predict any ADL behavior or activity for the user.

Accordingly, the "health state" of a particular user may depend greatly upon contextual factors, such as a correlation or relationship between the health state and ADLs/CDLs of the user, and other contextual factors such as defined by a user or learned via artificial intelligence. A deeper, cognitive analysis of the health state of one or more persons (e.g., patients) may be learned based on, for example, standards, rules, practices, and/or learned ADLs, CDLs, and/or other related behaviors or activities. In short, a cognitive learning process using artificial intelligence may learn each of the actions, decisions, ADLs, CDLs, behavior patterns of a user, a medical profile (which may include data relating to medical care or medical conditions), or other activities. Each learned health state may be saved as part of a user profile and/or retained in a knowledge domain. For example, the cognitive learning may learn preferred ADLs for particular priorities (e.g., brush teeth before leaving to work), preferences (dining at a particular restaurant), or even time periods (e.g., walking to work on warm, sunny days while taking a cab to work on rainy days).

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more medium/means. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
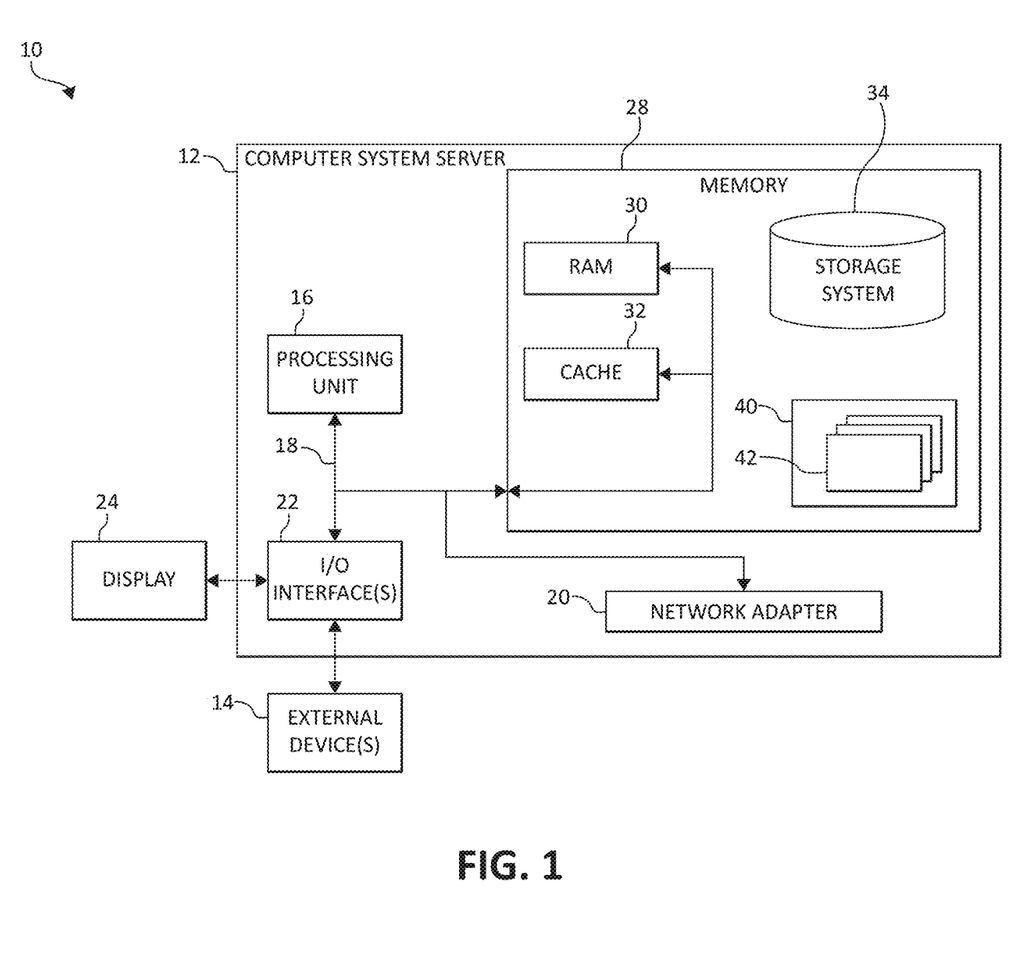
FIG. 1 is a block diagram depicting an exemplary computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
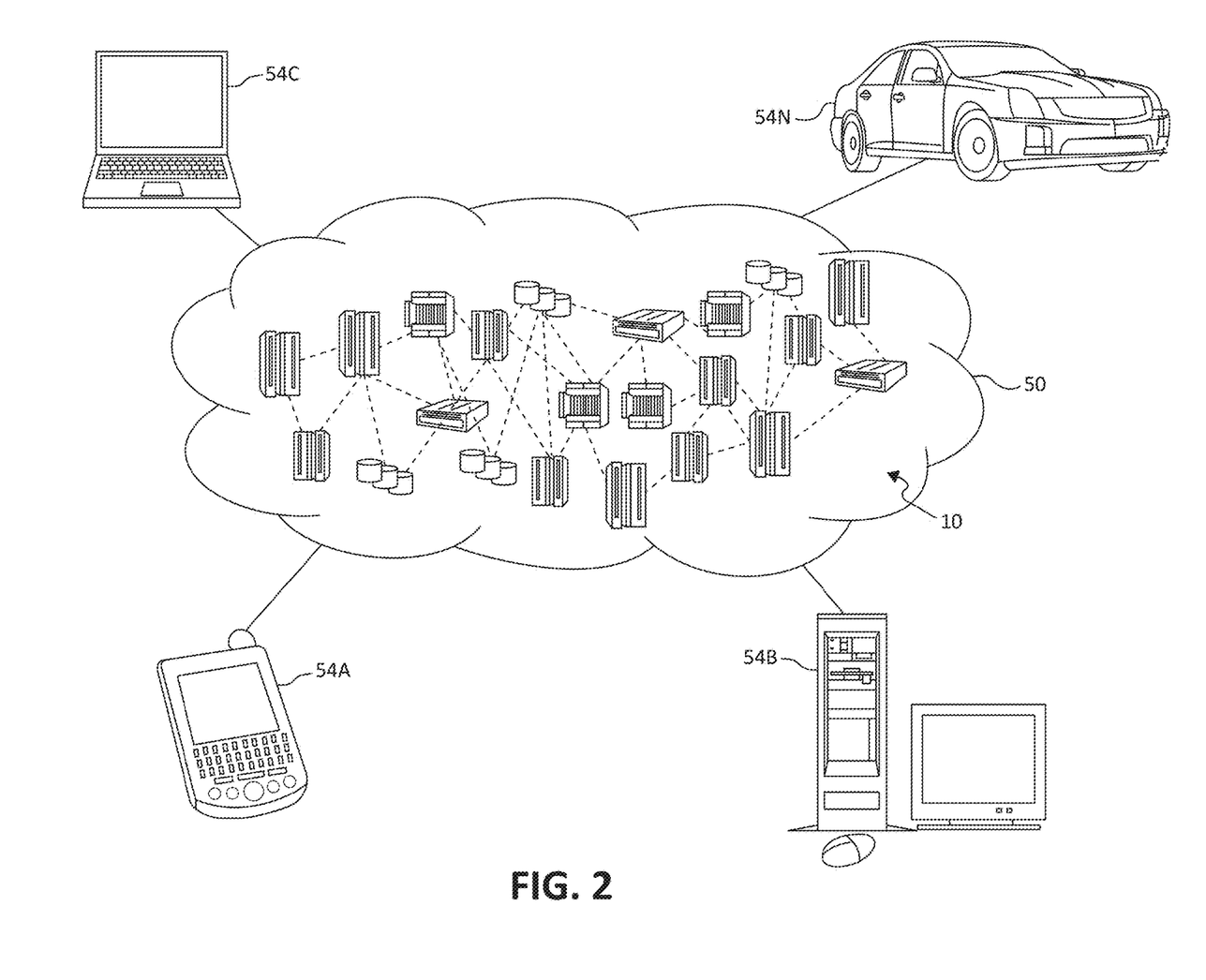
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
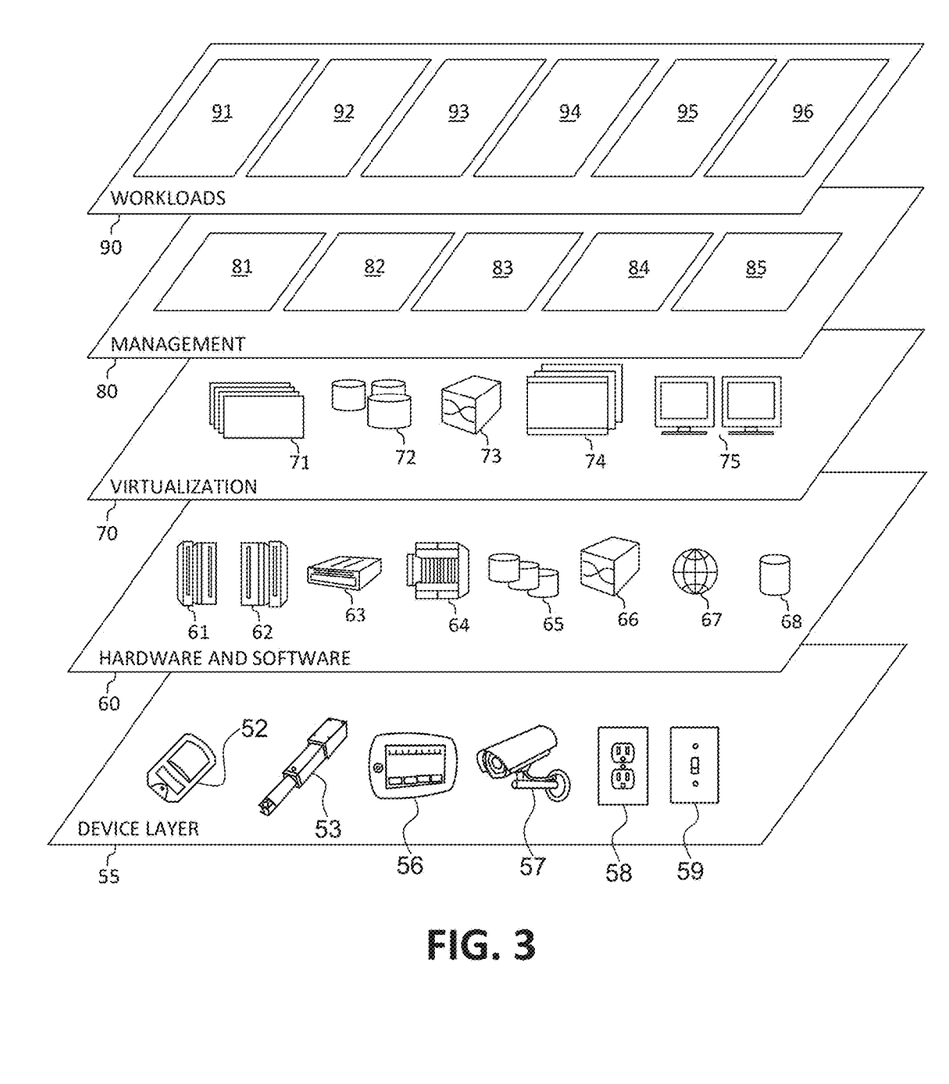
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent recommendation of useful medical actions. In addition, workloads and functions 96 for intelligent recommendation of useful medical actions may include such operations as data analytics, data analysis, and as will be further described, notification functionality. One of ordinary skill in the art will appreciate that the workloads and functions 96 for intelligent recommendation of useful medical actions may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for the intelligent recommendation of useful medical actions to a user using one or more processors. One or more medical actions may be cognitively recommended for impacting a health state of a user according to historical data collected from one or more data sources, one or more user profiles, a domain knowledge, feedback data, or a combination thereof.

In one aspect, for recommending the medical actions, the system for intelligent recommendation of useful medical actions includes receiving as input data one or more of the follow. 1) A patient current presentation profile (e.g., the actual symptoms) and/or a set of current or future courses of actions for that patient. 2) A patient clinical history (an electronic health record "EMR," etc.) and social or other relevant contextual history (e.g., ADL, sex, gender, other demographics, social determinants). 3) Historical data of one or more patients and treatments. 4) Historical data of feedback from one or more domain experts (e.g., medial professional such as, a medical doctor, nurse, administer, therapist, hospital staff members, laboratory personnel, etc.) and/or machine learning relating to one or more previous results computed by the intelligent recommendation of useful medical action system in similar cases. 5) A domain knowledge (e.g., a knowledge base/knowledge graphs, clinical documents, scientific literature, guidelines, a list of medications/drugs, side effects of the medications/drugs, clinical/medical research, or other defined data relating to a patient or group of patients). 6) Selected criteria of interest to provide a confidence score each recommendation such as, for example, a cost reduction function, score based on patient safety, or other set of defined criteria or parameters). In one aspect, as used herein, the medical actions may include a clinical action (e.g., an observation, diagnosis, and/or treatment of a patient), nursing activities, patient-care assistance, cleaning actions, actions impacting a health state of the user, or a combination thereof. The one or more useful medical actions may be refined according to the feedback data collected from a machine learning operation, a domain knowledge expert, or a combination thereof.

Using the input data, for recommending the useful medical actions, the system for intelligent recommendation of useful medical actions includes providing as output one or more recommended medical actions, which may also include a confidence score. In one aspect, the one or more recommended medical actions may be 1) a new recommended clinical action, 2) based on the recommendations of current or future courses of medical actions provided as input (e.g., scored accordingly to its usefulness, safety, cost, etc.). The confidence score may be based on a set of defined criteria indicating a) a level of usefulness the action is for the patient (e.g., treatments, medications, etc.), b) safety levels of the clinical action for a patient (e.g., how safe is the clinical action), c) a cost of the one or more medical actions, and/or a combination of a), b), and c).

Also, evidence data may be provided for each recommended clinical action. The evidence may comprise 1) a set of similar cases from other domain knowledge experts and/or machine learning operations (e.g., provide evidence for training less experienced medical staff), 2) a domain knowledge, and/or 3) historical data. In this way, the system for intelligent recommendation of useful medical actions assists healthcare professionals when dealing with patients, especially when time is critical, by providing real-time advice on usefulness of one or more clinical/medical actions, that may be suggested by medical professionals and/or machine learning, and recommending additional useful actions to reduce the overall cost, improve productivity of healthcare, and also protect the patients from unnecessary and unsafe actions.

Figure 4:
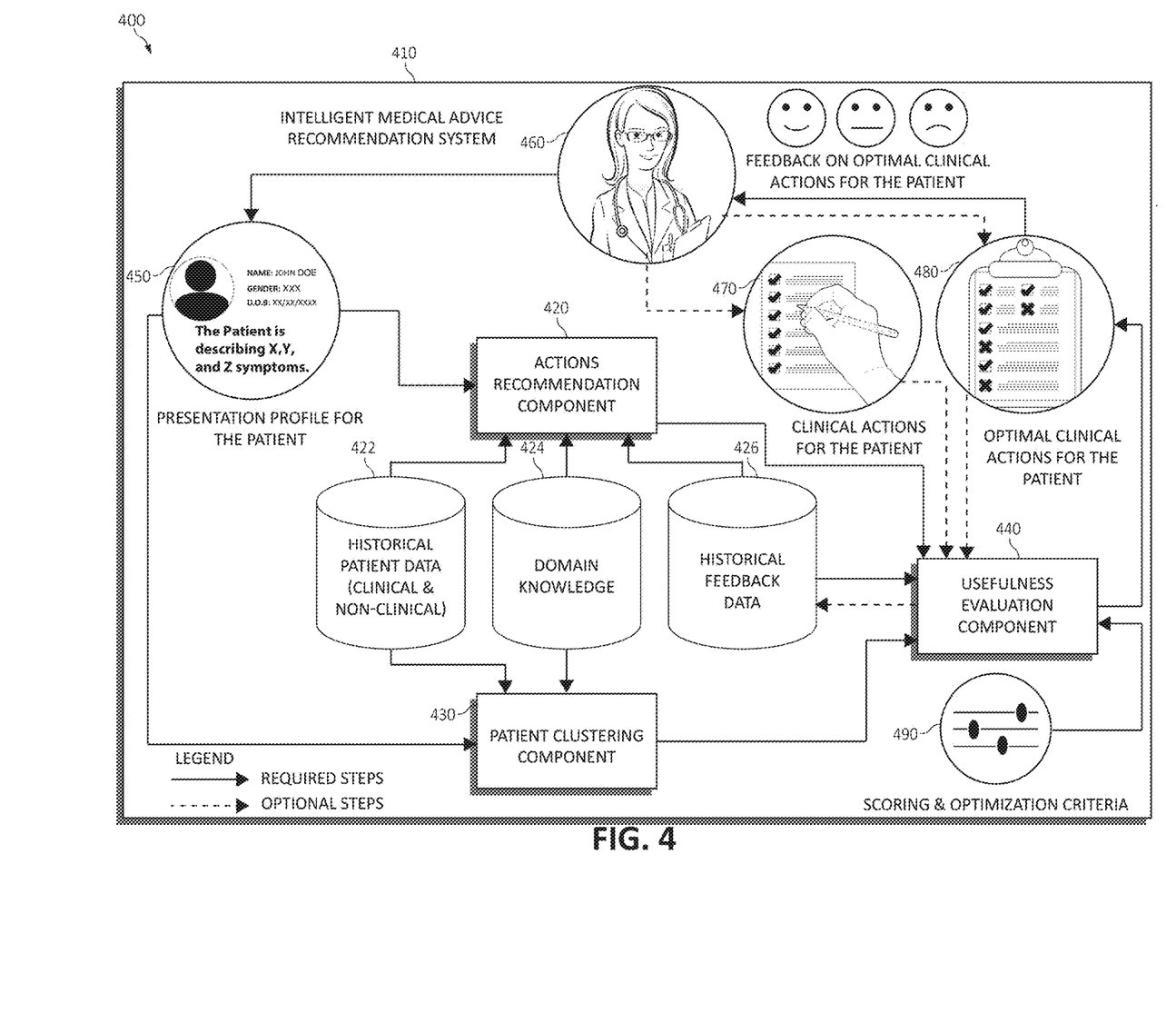
FIG. 4 is an additional block diagram depicting an exemplary functional relationship between various aspects of the present invention.

Turning now to FIG. 4, a block diagram depicting exemplary functional components 400 according to various mechanisms of the illustrated embodiments is shown. FIG. 4 illustrates intelligent recommendation of useful medical actions workloads and functions and training of a machine-learning model in a computing environment, such as a computing environment 402, according to an example of the present technology. As will be seen, many of the functional blocks may also be considered "modules" or "components" of functionality, in the same descriptive sense as has been previously described in FIGS. 1-3.

With the foregoing in mind, the module/component blocks of computing system 400 may also be incorporated into various hardware and software components of a system for intelligent recommendation of useful medical actions in accordance with the present invention. Many of the functional blocks 400 may execute as background processes on various components, either in distributed computing components, or on the user device, or elsewhere.

The computing system 400 may include an intelligent medical advice recommendation system 410. The intelligent medical advice recommendation system 410 may include an actions recommendation component 420, a patient clustering component 430, and a usefulness evaluation component 440. The actions recommendation component 420, patient clustering component 430, and the usefulness evaluation component 440 may each be in association/communication with historical patient data 422 (e.g., clinical and/or non-clinical data), a domain knowledge 424, and/or historical feedback data 426.

In one aspect, the intelligent medical advice recommendation system 410 may provide virtualized computing services (i.e., virtualized computing, virtualized storage, virtualized networking, etc.). More specifically, the intelligent medical advice recommendation system 410 may provide virtualized computing, virtualized storage, virtualized networking and other virtualized services that are executing on a hardware substrate.

In one aspect, the patient clustering component 430 may receive data relating to a patient presentation profile 450 (e.g., symptoms reported by a patient). The patient clustering component 430 may cluster patients based on named entities extracted from one or more data sources (e.g., a document/text such as notes from care workers) and other structured data (e.g., vitals, gender, age, etc.). In one aspect, the patient clustering component 430 may use a clustering operation such as, for example, K-Means clustering (or a variation thereof), or any other suitable clustering operation. The output patient clustering component 430 may be sent to and/or used by the usefulness evaluation component 440 to identify similar patients and/or (re)rank medical actions based on the cluster.

In one aspect, the actions recommendation component 420 may also receive data relating to the patient presentation profile 450 (e.g., symptoms reported by a patient). The actions recommendation component 420 recommends one or more useful medical actions 480 based on the patient presentation profile 450. That is, the actions recommendation component 420 cognitively recommend one or more useful medical actions 480 for impacting a health state of a user according to historical data 422 collected from one or more data sources, one or more user profiles (e.g., patient presentation profile 450, the domain knowledge 424, feedback data 426, or a combination thereof.

In one embodiment, the actions recommendation component 420 may use collaborative filtering. The actions recommendation component 420 may be trained on historical data 422 relating to one or more patients (both clinical and nonclinical), and feedback one or more optimal medical actions from the patient from one or more domain knowledge experts 460, which may include a machine learning operation learning the domain knowledge. The actions recommendation component 420 may use the domain knowledge 424 to improve, enhance and/or update the one or more clinical action recommendations.

The usefulness evaluation component 440 may rank and/or re-rank the one or more useful medical actions 480 to maximize a scoring criteria for determining a usefulness of the one or more useful medical actions 480, which a machine learning operation may be used. The machine learning operation may rank a set of medical actions by combining a given collection of ranking or preferences of the medical actions. In one aspect, scoring criteria may include, but not limited, to a determination of how useful and/or necessary an action (e.g., treatment, medication, etc.) based on statistical analysis of historically similar cases, how safe and/or effective an action is on the patient (e.g., action that positively affects the health state of the user) based on patient data and/or the statistical analysis of historically similar cases, and/or a financial cost/constraint of the action is upon the patient. The scoring criteria may be assigned a value such as, for example a percentage and/or a value within a range of values.

In one aspect, if a care worker/medical professional (e.g., domain knowledge expert 460) has provided medical actions 470 as input, the usefulness evaluation component 440 may merge the medical actions 470 provided by the care giver with the recommended medical actions 480 determined by the actions recommendation component 420. The ranking of the one or more useful medical actions 480 may be determined and/or computed based on configurable scoring criteria 490, the domain knowledge 424, and feedback data 426 (e.g., historical feedback data) from the domain knowledge experts 460 about previously computed results.

The usefulness evaluation component 440 may use a set of rules to boost medical actions 480 that are more important as compared to other possible medical actions, and to assign a negative score to the one or more useful medical actions 480 that are known to be ineffective and/or unsafe in that particular context. For example, the set of rules may include, but not limited to, assigning a positive, normalized score (e.g., confidence score) to a medical action if the outcome of the medical action applied to previous cases was successful. The confidence score may be increased for those cases having a greater similarity to the user (e.g., a confidence score may have a greater weight, rank, and/or percentage for success on the user)

In one aspect, cognitively recommending one or more useful medical actions for impacting a health state of a user (or machine learning modeling), as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the intelligent medical advice recommendation system 410 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

In view of the functions and operations of computing system 400 of FIG. 4, consider the following example. Assume a 40 year-old male patient presents persistent flu-like symptoms (e.g., raised temperature and heart rate, weakness and fatigue) and arrhythmia to an emergency department ("ED"). After an initial ED triage assessment carried out by staff, the staff recommendation is that the patient should undergo a full cardiology assessment. At this point, the present invention may use the patient clustering component 430 to locate and learn information about a) initial presentation and patient history that two weeks ago the patient had presented to a general practitioner's ("GP") office with similar symptoms, but also hypotension and confusion and was sent home with a pain relief drug (e.g., paracetamol). The patient clustering component 430 learns information about previous patients with similar presentations (e.g., symptoms) where the similar patients admitted to ED each had a full blood count (FBC) performed. In short, the patient clustering component 430 may use a presentation profile of the 40 year-old male patient to identify one or more similar patients.

Feedback from one or more domain knowledge experts 460 may be from local ED experts having suggested that all ED admissions with potential infections should be further evaluated for sepsis. The domain knowledge may be used (e.g., information appears in a sepsis diagnostic criteria and this criteria suggests additional tests such as, for example, lactate should be performed). Said differently, the patient clustering component 430 retrieves data from the historical feedback data 426.

At the ED triage, the actions recommendation component 420 may recommend that a lactate blood test and another test for infection (INR) is undertaken to assess for sepsis and organ injury as this takes higher priority. The results of these tests reveal high lactate (e.g., organ damage) and is likely to be caused by the underlying sepsis. The actions recommendation component 420 prevents an unnecessary cardiology assessment. The actions recommendation component 420 recommends one or more useful medical actions such as, for example, a test based on local feedback and domain knowledge. The actions recommendation component 420 also outputs a set of similar cases with explanation to the junior staff at the ED so that the junior staff can make a better, more informed and effective decision for the patient. The actions recommendation component 420 recommends a patient to be started on fluids as soon as possible. That is, the actions recommendation component 420 may use collaborative filtering to recommend the most appropriate actions for the patient. Feedback from domain knowledge experts, machine learning operations, and filter and/or augment the one or more recommended medical actions.

Figure 5:
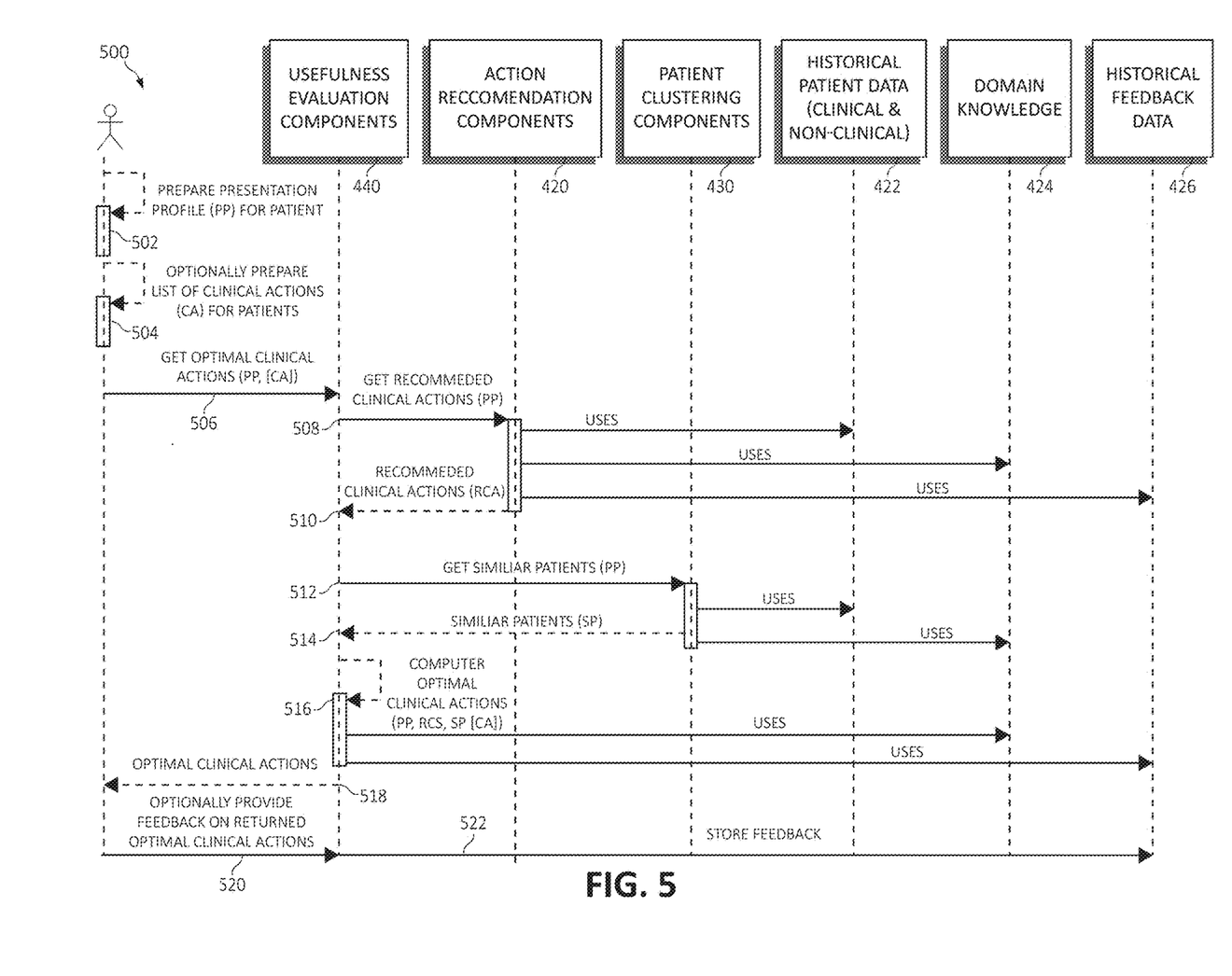
FIG. 5 is an additional flowchart diagram depicting an additional exemplary method for intelligent recommendation of useful medical actions in which aspects of the present invention may be realized.

Turning now to FIG. 5, a block diagram of exemplary functionality 600 of an intelligent recommendation of useful medical actions is depicted. It should be noted that the intelligent medical advice recommendation system 410 may be included in and/or associated with computer system/server 12 of FIG. 1, incorporating one or more processing unit(s) 16 to perform various computational, data processing and other functionality in accordance with various aspects of the present invention. For example, functionality 500 of the intelligent medical advice recommendation system 410 is illustrated using the recommendation component 420, the patient clustering component 430, the usefulness evaluation component 440, the historical patient data 422, the domain knowledge 424, and/or the feedback data 426.

As shown, the various blocks of functionality are depicted with arrows designating the blocks' 500 relationships with each other and to show process flow of the intelligent medical advice recommendation system 410. Additionally, descriptive information is also seen relating each of the functional blocks 500. As will be seen, many of the functional blocks may also be considered "modules" or "components" of functionality, in the same descriptive sense as has been previously described in FIGS. 1-5. With the foregoing in mind, the module blocks 600 may also be incorporated into various hardware and software components of a system for image enhancement in accordance with the present invention. Many of the functional blocks 600 may execute as background processes on various components, either in distributed computing components, or on the user device, or elsewhere, and generally unaware to the user performing generalized tasks of the present invention.

Starting with block 502, a patient presentation profile ("PP") may be prepared for a patient. Also, a list of medical actions ("CA") may be prepared, optionally, for the patient, as in block 504. A request may be issued to the usefulness evaluation component 440 to retrieve one or more optimized medical actions (using the PP, CA), as in block 506. The usefulness evaluation component 440 sends a request to the recommendation component 420 to retrieve one or more useful medical actions for the PP, as in block 508. The recommendation component 420 access the historical patient data 422, the domain knowledge 424, and/or the feedback data 426 and recommends one or more useful medical actions ("RCA") to the usefulness evaluation component 440, as in block 510. The usefulness evaluation component 440 sends a request to the patient clustering component 430 to request similar patient presentation profiles ("SP") relating to the patient, as in block 512. The patient clustering component 430 accesses the historical patient data 422 and the domain knowledge 424, collects the similar patient presentation profiles ("SP"), and returns the results to the usefulness evaluation component 440, as in block 514.

The usefulness evaluation component 440 may determine and/or compute one or more useful medical actions (according to the PP, RCA, and/or SP), which may include accessing the domain knowledge 424 and the feedback data 426, as in block 516. That is, the one or more useful medical actions may be optimized medical actions for a specific patient based on the patient's symptoms (e.g., presentation profile), the recommended medical actions, profile data from similar patients having similar symptoms, and/or a ranked order of RCA's. The usefulness evaluation component 440 provides the one or more optimal medical actions to a user (e.g., medical professional/care giver), as in block 518. Additionally, feedback data on the one or more optimal medical actions may be provided to and/or received by the usefulness evaluation component 440, as in block 520. The feedback data may be stored with the feedback data 426, as in block 522.

Thus, the intelligent medical advice recommendation system 410 may compute optimally useful medical actions for a patient. In one aspect, "optimally useful medical actions" may refer to one or more medical actions that may have a most positive impact upon the health state of a patient as compared to other medical actions. The medical actions may include, for example, treatments, lab tests, assessments, routines, medications, or other actions that positively impact the health state of the patient. The medical actions maximize usefulness according to a set of scoring criteria, and the optimal medical actions may be combined with medical actions decided by a domain knowledge expert. When domain knowledge expert decides on one or more medical actions for a patient, the intelligent medical advice recommendation system 410 can interactively include additional and/or alternative medical actions to maximize usefulness according to the set of scoring criteria. The computed medical actions may be ranked. For example, medical actions having a more positive impact on the health state of a patient may be ranked higher than those medical actions having less positive (or negative) impact on the health state of the user.

The ranking uses and/or leverages (1) clinical and non-clinical historical data about the patient and similar patients, (2) feedback from experts about previous similar cases, and (3) domain knowledge. The historical data may include, for example, EMRs, clinical data, historical (non-medical) contextual data (e.g., social data, habits, ADLs, or other non-medical/clinical data). The feedback may be collected from domain knowledge experts (which may include using a machine learning operation to learn the domain knowledge) about previous similar cases of the patient, which may include, for example, acceptance and/or rejection of previous suggestions, scoring of previous suggestions (e.g., 1-5 rating). The usefulness functions of the usefulness evaluation component 440 may include patient safety, and costs of medical actions.

Figure 6:
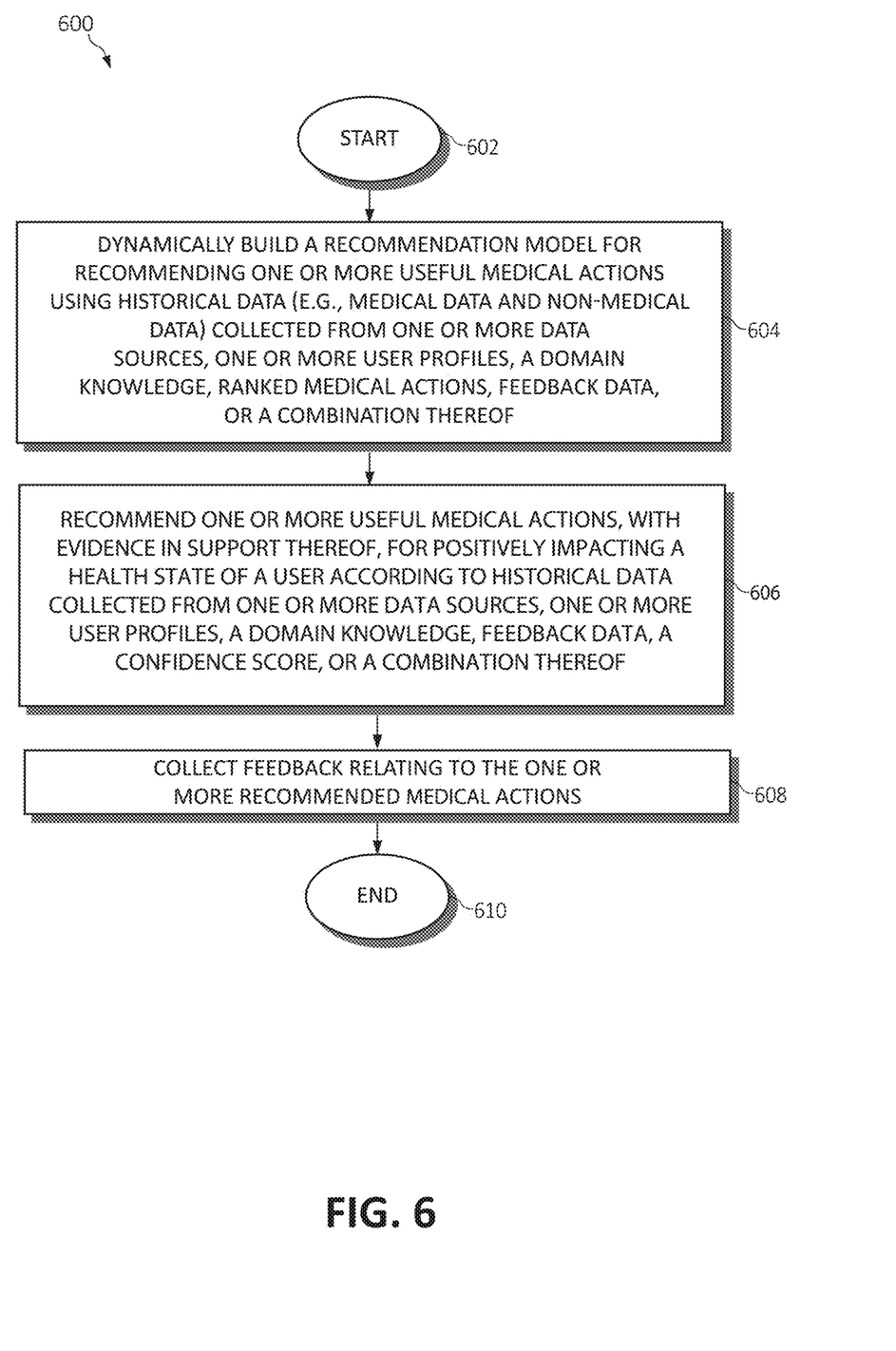
FIG. 6 is an additional flowchart diagram depicting an additional exemplary method for intelligent recommendation of useful medical actions by a processor, again in which aspects of the present invention may be realized.

Turning now to FIG. 6, a method 600 for generating personalized advice by a processor is depicted, in which various aspects of the illustrated embodiments may be implemented. The functionality 600 may be implemented as a method executed as instructions on a machine, where the instructions are included on at least one computer readable medium or one non-transitory machine-readable storage medium. The functionality 600 may start in block 602.

Dynamically build a recommendation model for recommending the one or more useful medical actions using historical data (e.g., medical data and non-medical data) collected from one or more data sources, one or more user profiles, a domain knowledge, ranked medical actions, feedback data, or a combination thereof, as in block 604. One or more useful medical actions may be recommended, with evidence in support thereof, for positively impacting a health state of a user according to historical data collected from one or more data sources, one or more user profiles, a domain knowledge, feedback data, a confidence score, or a combination thereof, as in block 606. The evidence may include, but not limited to, a set of similar cases from other patients, domain experts (e.g., cases of other medical doctors/professionals), domain knowledge, and/or past history. Feedback relating to the one or more recommended medical actions may be collected, as in block 608. The functionality 600 may end, as in block 610.

In one aspect, in conjunction with and/or as part of at least one block of FIG. 6, the operations of method 600 may include each of the following. The operations of method 600 may cognitively reason and interact with a patient, domain knowledge expert, and/or machine learning operations for collecting the feedback information. The operations of method 600 may refine, update, adjust, and/or modify the recommendation model for recommending the one or more useful medical actions according to the feedback data collected from a machine learning operation, a domain knowledge expert, or a combination thereof.

The operations of method 600 may suggest one or more useful medical actions as an alternative to one or more useful medical actions provided by a domain knowledge expert for the user, and/or enhancing one or more alternative medical actions and/or usefulness of one or more clinical/medical actions provided by a domain knowledge expert for the user using the one or more medical actions, with the evidence in support thereof.

The one or more useful medical actions may be ranked according to a scoring criteria, the domain knowledge, the historical data, a set of rules, previously recommended medical actions, or a combination thereof. A confidence score may be assigned to the one or more useful medical actions indicating an effectiveness and safety upon the health state of the user (e.g., a positive or negative impact upon the health state of the patient). The operations of method 700 may initialize a machine learning mechanism to learn, approve, reject, rank, or recommend the one or more useful medical actions.

In an additional aspect, the operations of method 600 may also include initializing a machine learning mechanism using the feedback information to learn the health state. The health state may include at least one or more medical conditions, a subjective health state (SWB) of the user, social or contextual data of one or more users, an emotional state of the user, biometric data, behavior patterns, a health profile of the user, or a combination thereof The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for intelligent recommendation of useful medical actions by a processor, comprising:
receiving a patient presentation profile indicating symptoms of a patient and an initial list of medical actions of a set of current courses of action issued by a medical professional for the patient;
receiving information from a domain knowledge, historical data relating to medical and non-medical data collected from a plurality of patients including the patient, and feedback data of an outcome of the set of current or future courses of action in alternative patients having the symptoms;
generating an initial list of one or more useful medical actions according to the information from the domain knowledge, the historical data, and the feedback data;
training a machine learning model, in a machine learning operation, using the initial list of one or more useful medical actions, the information from the domain knowledge, the historical data, and the feedback data as input, wherein the machine learning model partitions the plurality of patients according to respective patient presentation profiles of each into a plurality of clusters using a k-means clustering algorithm;
determining those of the plurality of patients in the plurality of clusters having most similar symptoms to the patient, and identifying respective treatments thereof;
generating an optimized list of the one or more useful medical actions, with evidence in support thereof, that positively impact a health state of the patient according to an analyzation of the information from the domain knowledge, the historical data, the feedback data, and the respective treatments of those of the plurality of patients having the most similar symptoms to the patient, wherein the one or more useful medical actions are each associated with a confidence score such that the optimized list includes reordered ones of the one or more useful medical actions on the initial list in addition to new courses of action not presented on the initial list, based on the confidence score as output from the trained machine learning model; and
as part of reordering the ones of the one or more useful medical actions on the optimized list, prioritizing those of the one or more useful medical actions known, when administered to the patient and observed to produce a particular outcome, to render others of the one or more useful medical actions originally included in the initial list of medical actions unnecessary only when the particular outcome is observed, notwithstanding the others of the one or more useful medical actions rendered unnecessary would otherwise be appropriate for at least some of the symptoms; and
in conjunction with receiving the feedback, receiving an input of scoring of those of the ones of the one or more useful medical actions on the optimized list by the medical professional, and re-training the machine learning model using the input of scoring to optimize future suggested courses of action for those of the plurality of patients having the most similar symptoms to the patient.

2. The method of claim 1, further including refining the initial list of the one or more useful medical actions according to the feedback data collected from the machine learning operation, a domain knowledge expert, or a combination thereof.

3. The method of claim 1, further including:
suggesting the one or more useful medical actions as an alternative to one or more useful medical actions provided by a domain knowledge expert for the patient; or
enhancing an alternative medical action provided by the domain knowledge expert for the patient using the one or more useful medical actions, with the evidence in support thereof.

4. The method of claim 1, further including ranking the one or more useful medical actions according to a scoring criteria, the domain knowledge, the historical data, a set of rules, previously recommended medical actions, or a combination thereof.

5. The method of claim 1, further including assigning the confidence score to the one or more useful medical actions indicating an effectiveness and safety upon the health state of the patient.

6. The method of claim 1, further including initializing the machine learning operation to learn, approve, reject, rank, or recommend the one or more useful medical actions and the evidence, wherein the evidence includes a set of similar cases from the plurality of patients, domain experts, the domain knowledge, the historical data, or a combination thereof.

7. A system for intelligent recommendation of useful medical actions, comprising:
one or more computers with executable instructions that when executed cause the system to:
receive a patient presentation profile indicating symptoms of a patient and an initial list of medical actions of a set of current courses of action issued by a medical professional for the patient;
receive information from a domain knowledge, historical data relating to medical and non-medical data collected from a plurality of patients including the patient, and feedback data of an outcome of the set of current or future courses of action in alternative patients having the symptoms;
generate an initial list of one or more useful medical actions according to the information from the domain knowledge, the historical data, and the feedback data;
train a machine learning model, in a machine learning operation, using the initial list of one or more useful medical actions, the information from the domain knowledge, the historical data, and the feedback data as input, wherein the machine learning model partitions the plurality of patients according to respective patient presentation profiles of each into a plurality of clusters using a k-means clustering algorithm;

determine those of the plurality of patients in the plurality of clusters having most similar symptoms to the patient, and identifying respective treatments thereof;

generate an optimized list of the one or more useful medical actions, with evidence in support thereof, that positively impact a health state of the patient according to an analyzation of the information from the domain knowledge, the historical data, the feedback data, and the respective treatments of those of the plurality of patients having the most similar symptoms to the patient, wherein the one or more useful medical actions are each associated with a confidence score such that the optimized list includes reordered ones of the one or more useful medical actions on the initial list in addition to new courses of action not presented on the initial list, based on the confidence score as output from the trained machine learning model;

as part of reordering the ones of the one or more useful medical actions on the optimized list, prioritize those of the one or more useful medical actions known, when administered to the patient and observed to produce a particular outcome, to render others of the one or more useful medical actions originally included in the initial list of medical actions unnecessary only when the particular outcome is observed, notwithstanding the others of the one or more useful medical actions rendered unnecessary would otherwise be appropriate for at least some of the symptoms; and in conjunction with receiving the feedback, receive an input of scoring of those of the ones of the one or more useful medical actions on the optimized list by the medical professional, and re-train the machine learning model using the input of scoring to optimize future suggested courses of action for those of the plurality of patients having the most similar symptoms to the patient.

8. The system of claim 7, wherein, pursuant to recommending one or more useful medical actions, the executable instructions further refine the initial list of the one or more useful medical actions according to the feedback data collected from the machine learning operation, a domain knowledge expert, or a combination thereof.

9. The system of claim 7, wherein the executable instructions further:

suggest the one or more useful medical actions as an alternative to one or more useful medical actions provided by a domain knowledge expert for the patient; or enhance an alternative medical action provided by the domain knowledge expert for the patient using the one or more useful medical actions, with the evidence in support thereof.

10. The system of claim 7, wherein the executable instructions further rank the one or more useful medical actions according to a scoring criteria, the domain knowledge, the historical data, a set of rules, previously recommended medical actions, or a combination thereof.

11. The system of claim 7, wherein the executable instructions further assign the confidence score to the one or more useful medical actions indicating an effectiveness and safety upon the health state of the patient.

12. The system of claim 7, wherein the executable instructions further initialize the machine learning operation to learn, approve, reject, rank, or recommend the one or more useful medical actions and the evidence, wherein the evidence includes a set of similar cases from the plurality of patients, domain experts, the domain knowledge, the historical data, or a combination thereof.

13. A computer program product for intelligent recommendation of useful medical actions by a processor, the computer program product comprising a non-transitory computer-readable storage medium having computer-readable program code portions stored therein, the computer-readable program code portions comprising:

an executable portion that receives a patient presentation profile indicating symptoms of a patient and an initial list of medical actions of a set of current courses of action issued by a medical professional for the patient;

an executable portion that receives information from a domain knowledge, historical data relating to medical and non-medical data collected from a plurality of patients including the patient, and feedback data of an outcome of the set of current or future courses of action in alternative patients having the symptoms;

an executable portion that generates an initial list of one or more useful medical actions according to the information from the domain knowledge, the historical data, and the feedback data;

an executable portion that trains a machine learning model, in a machine learning operation, using the initial list of one or more useful medical actions, the information from the domain knowledge, the historical data, and the feedback data as input, wherein the machine learning model partitions the plurality of patients according to respective patient presentation profiles of each into a plurality of clusters using a k-means clustering algorithm;

an executable portion that determines those of the plurality of patients in the plurality of clusters having most similar symptoms to the patient, and identifying respective treatments thereof;

an executable portion that generates an optimized list of the one or more useful medical actions, with evidence in support thereof, that positively impact a health state of the patient according to an analyzation of the information from the domain knowledge, the historical data, the feedback data, and the respective treatments of those of the plurality of patients having the most similar symptoms to the patient, wherein the one or more useful medical actions are each associated with a confidence score such that the optimized list includes reordered ones of the one or more useful medical actions on the initial list in addition to new courses of action not presented on the initial list, based on the confidence score as output from the trained machine learning model;

an executable portion that, as part of reordering the ones of the one or more useful medical actions on the optimized list, prioritizes those of the one or more useful medical actions known, when administered to the patient and observed to produce a particular outcome, to render others of the one or more useful medical actions originally included in the initial list of medical actions unnecessary only when the particular outcome is observed, notwithstanding the others of the one or more useful medical actions rendered unnecessary would otherwise be appropriate for at least some of the symptoms; and an executable portion that, in conjunction with receiving the feedback, receives an input of scoring of those of the ones of the one or more useful medical actions on the optimized list by the medical professional, and re-trains the machine learning model using the input of scoring to optimize future suggested courses of action for those of the plurality of patients having the most similar symptoms to the patient.

14. The computer program product of claim 13, further including, pursuant to recommending one or more useful medical actions, an executable portion that refines the initial list of the one or more useful medical actions according to the feedback data collected from the machine learning operation, a domain knowledge expert, or a combination thereof.

15. The computer program product of claim 13, further including an executable portion that:
   suggests the one or more useful medical actions as an alternative to one or more useful medical actions provided by a domain knowledge expert for the patient; or
   enhances an alternative medical action provided by the domain knowledge expert for the patient using the one or more useful medical actions, with the evidence in support thereof.

16. The computer program product of claim 13, further including an executable portion that:
   ranks the one or more useful medical actions according to a scoring criteria, the domain knowledge, the historical data, a set of rules, previously recommended medical actions, or a combination thereof; and
   assigns the confidence score to the one or more useful medical actions indicating an effectiveness and safety upon the health state of the patient.

17. The computer program product of claim 13, further including an executable portion that initializes the machine learning operation to learn, approve, reject, rank, or recommend the one or more useful medical actions and the evidence, wherein the evidence includes a set of similar cases from the plurality of patients, domain experts, the domain knowledge, the historical data, or a combination thereof.

* * * * *